US009421292B2

United States Patent
Parker et al.

(10) Patent No.: US 9,421,292 B2
(45) Date of Patent: Aug. 23, 2016

(54) CONDITIONING MEDICAL EQUIPMENT (75) Inventors: George Christopher Parker, Westcliff-on-Sea (GB); Barry Luke, Canvey Island (GB); Colin Oxford, Canvey Island (GB)

(73) Assignee: Cantel (UK) Limited, Southend-on-Sea, Essex (GB)

( * ) Notice: Subject to any disclaimer, the term of this patent is extended or adjusted under 35 U.S.C. 154(b) by 705 days.

(21) Appl. No.: 13/822,663

(22) PCT Filed: Aug. 30, 2011

(86) PCT No.: PCT/GB2011/051623
§ 371 (c)(1),
(2), (4) Date: Apr. 23, 2013

(87) PCT Pub. No.: WO2012/035313
PCT Pub. Date: Mar. 22, 2012

(65) Prior Publication Data
US 2013/0205720 A1  Aug. 15, 2013

(30) Foreign Application Priority Data

Sep. 15, 2010 (GB) .................................. 1015400.3
Sep. 15, 2010 (GB) .................................. 1015422.7
Jul. 6, 2011 (GB) .................................. 1111524.3

(51) Int. Cl.
*A61L 2/18* (2006.01)
*A61B 1/00* (2006.01)
(Continued)

(52) U.S. Cl.
CPC ............. *A61L 2/186* (2013.01); *A61B 1/00144* (2013.01); *A61B 1/015* (2013.01); *A61B 1/123* (2013.01); *A61B 1/125* (2013.01); *A61B 2017/00199* (2013.01); *A61B 2050/3005* (2016.02); *A61B 2050/314* (2016.02); *A61L 2/18* (2013.01); *A61L 2202/181* (2013.01); *A61L 2202/24* (2013.01)

(58) Field of Classification Search
CPC ............................... A61B 1/125; A61L 2/286
USPC .................. 53/425, 167; 134/95; 422/116
See application file for complete search history.

(56) References Cited

U.S. PATENT DOCUMENTS 4,064,886 A * 12/1977 Heckele ................. A61B 1/125
134/102.1
4,526,622 A * 7/1985 Takamura ............... A61B 1/125
134/21
(Continued)

*Primary Examiner* — Nathaniel Chukwurah
(74) *Attorney, Agent, or Firm* — Sorell, Lenna & Schmidt LLP; William D. Schmidt, Esq.

(57) ABSTRACT

A method for conditioning a flexible medical endoscope (10) having internal channels (12), so as to maintain disinfection of said endoscope (10) following processing to a state of high level disinfection, comprises the steps of:
(a) connecting the internal channels (12) of the endoscope (10) to connectors (31-34) enabling fluid communication with a reservoir (24) of disinfectant fluid (25);
(b) charging the internal channels (12) with disinfectant fluid (25) from the reservoir (24);
(c) disconnecting the internal channels (12) from the connectors (31-34);
(d) sealing the endoscope (10) in a pouch (56) having a substantially air-tight seal (57) and a valve (55) enabling connection to suction means (53); and
(e) connecting and activating the suction means (53) so as substantially to reduce pressure within the pouch (56), thereby partially evacuating the pouch (56).

13 Claims, 5 Drawing Sheets

(51) Int. Cl.
*A61B 1/015* (2006.01)
*A61B 1/12* (2006.01)
*A61B 17/00* (2006.01)

(56) References Cited

U.S. PATENT DOCUMENTS

| | | | | |
|---|---|---|---|---|
| 5,288,467 A | * | 2/1994 | Biermaier | A61L 2/26 134/170 |
| 5,534,221 A | * | 7/1996 | Hillebrenner | A61L 2/26 206/438 |
| 5,580,530 A | * | 12/1996 | Kowatsch | A61B 1/121 220/278 |
| 6,312,645 B1 | * | 11/2001 | Lin | A61B 1/121 422/28 |
| 6,534,002 B1 | | 3/2003 | Lin et al. | |
| 2009/0512333 | | 5/2009 | Yamada Akifumi et al. | |
| 2010/0224222 A1 | | 9/2010 | Vedovelli | |
| 2011/0192744 A1 | | 8/2011 | Parker et al. | |

* cited by examiner

CONDITIONING MEDICAL EQUIPMENT

This invention relates to a method for conditioning medical equipment following processing (cleaning and disinfection) of said equipment, and to apparatus for use in such a method. In particular, the invention relates to a method and apparatus for conditioning a flexible medical endoscope, following processing of said endoscope to a state of high level disinfection.

The term "disinfection" is used herein in preference to the term "sterility" since the latter implies the complete absence of pathogenic organisms, which in practice is rarely, if ever, achievable. It is to be appreciated however that the ultimate aim of disinfecting medical equipment is indeed to get as close to absolute sterility as is practicable. The term "conditioning" is used herein to refer to a method of maintaining the disinfection of medical equipment following processing thereof to a state of high level disinfection The present invention has been developed in connection with the processing and storage of flexible medical endoscopes, and therefore will be described herein with particular emphasis on this application. It is envisaged however, that the method of the present invention may be applied to the processing and storage of substantially all types of medical, surgical, dental and veterinary equipment, apparatus, and instruments.

After use in an endoscopic procedure, flexible medical endoscopes are usually subjected to "processing", consisting of rigorous manual cleaning followed by placing the endoscope in an Automated Endoscope Re-processor (AER) which effects a further cleaning and disinfecting procedure to bring the endoscope to a High Level Disinfection Status (HLDS). The endoscope is then stored in a clean environment. Under normal storage conditions, the degree of disinfection of the endoscope can only be maintained at an acceptable level for a relatively short period, usually about 3 hours. This is due to the multiplication of residual pathogens which may remain on the endoscope after disinfection, or which may be present in the atmosphere. If the endoscope is not used in a further endoscopic procedure within this time, then further processing will be necessary prior to its next use. Frequent and repeated processing is undesirable, since it reduces the availability of the endoscope for endoscopic procedures, whilst increasing the operating costs, due to the need for cleaning and disinfectant materials and the operation of cleaning equipment. Furthermore, repeated processing reduces the lifetime of the endoscope due to wear and tear.

The loss of HLDS over the 3 hour storage period is due to the inability of the AER completely to dry the internal channels of the endoscope, due to the small internal diameter of these channels. The residual moisture within the channels provides an environment in which micro-organisms can quickly multiply.

Previous attempts to prolong the period for which processed endoscopes can be maintained at HLDS have therefore tended to focus on drying the internal channels of the processed endoscope. Endoscope drying cabinets have therefore been developed, which involve the circulation of dry filtered air around the endoscope and through the internal channels to drive out residual moisture. However, these drying cabinets are very large, bulky—and expensive—articles, which do not lend themselves well to use in hospital departments where space is likely to be at a premium. Consequently, such cabinets are likely to be located some distance away from the procedure room or operating theatre in which the endoscope is to be used, leading to a risk of loss of HLDS on the journey between the drying cabinet. Further drawbacks associated with the use of drying cabinets include the risk of cross-contamination as a result of multiple endoscopes being stored together in the cabinets in close proximity, and the risk of contamination entering the cabinet from the external atmosphere each time the cabinet door is opened.

The genesis of the present invention stems from the realisation that all of the above shortcomings of drying cabinets can be avoided by developing a method and apparatus which does not seek to remove the residual moisture from the internal channels of the endoscope, but rather seeks to replace this residual rinse water with an effective disinfectant within the internal channels.

Methods and apparatus for maintaining and prolonging the disinfection of flexible medical endoscopes are disclosed in the applicant's International Publications Nos. WO 2007/049076 and WO 2010/046617. The present invention represents a further evolution and improvement of the methods and apparatus disclosed in those prior art references.

According to a first aspect of the present invention, there is provided a method for conditioning a flexible medical endoscope having internal channels, so as to maintain disinfection of said endoscope following processing to a state of high level disinfection, said method comprising the steps of:

(a) connecting the internal channels of the endoscope to connectors enabling fluid communication with a reservoir of disinfectant fluid;

(b) charging the internal channels with disinfectant fluid from the reservoir;

(c) disconnecting the internal channels from the connectors;

(d) sealing the endoscope in a pouch having a substantially air-tight seal and a valve enabling connection to suction means; and (e) connecting and activating said suction means so as substantially to reduce pressure within the pouch, thereby partially evacuating said pouch.

Step (b) preferably further comprises the sub-step of:

(b)(i) following charging of the internal channels with disinfectant fluid, flushing the internal channels with pressurised filtered air so as to expel disinfectant fluid from said internal channels.

The pouch utilised in step (d) preferably has two substantially air-tight seals, which may utilise plastic zip fasteners and/or an adhesive closure strip.

The method of the present invention is preferably carried out on or at a conditioning station housing the disinfectant fluid reservoir and the suction means. The conditioning station preferably further comprises a processor adapted to control steps (b) and (e) according to a pre-programmed sequence.

In preferred embodiments of the method of the present invention, a printed label is generated and applied to the pouch following step (e). The label may identify the endoscope, its disinfection status, and the estimated maximum disinfection maintenance period. The conditioning station preferably further houses a printer in communication with the processor, for generation of the printed label.

The disinfectant fluid is preferably a dilute aqueous solution of hydrogen peroxide. More preferably, the dilute aqueous solution of hydrogen peroxide has a concentration in the range of from 0.5% to 1.5% by weight; and most preferably has a concentration of substantially 1.4% by weight. The disinfectant fluid preferably further comprises colloidal silver.

The endoscope is preferably housed within a moulded tray shaped to accommodate the endoscope, so as to protect against compression of the endoscope channels during step (e).

It should be noted that, although steps (a) to (c) may be carried out with the endoscope already located in an open pouch, it is generally preferred that the endoscope is placed into the pouch between steps (c) and (d). Similarly, where the moulded tray is utilised, the endoscope may be located in the tray during the performance of steps (a) to (c), or alternatively, the endoscope may be placed into the tray after step (c), with the endoscope and tray both then being placed into the pouch prior to step (d).

An absorbent pad may preferably be placed in the pouch together with the endoscope, said pad being arranged to collect disinfectant fluid expelled from the endoscope channels. The expulsion of disinfectant fluid from the endoscope channels may be effected by the air flushing sub-step (b)(i) if present, and/or may occur as a consequence of the pressure reduction step (e). The pressure reduction step (e) also causes evaporation of disinfectant fluid from the pad into the pouch, enabling coating of the external surfaces of the endoscope with the disinfectant fluid, thus providing a further disinfectant effect for the duration of the period for which the endoscope is stored within the partially evacuated pouch.

Following performance of step (e), the pouch is preferably housed within a rigid case to provide protection during transit.

The method of the present invention is intended primarily for use with flexible medical endoscopes having a plurality of internal channels, comprising an air channel, a water channel and an aspiration channel. It is therefore preferable that, in step (a), each of said channels is connected to an individual dedicated connector in communication with the fluid reservoir. In such embodiments of the method of the present invention, in step (b) each of said channels is preferably charged in turn with disinfectant fluid, according to a pre-determined sequence.

The scope of the present invention extends to encompass apparatus for use in the performance of the method according to the first aspect of the present invention.

Therefore, according to a second aspect of the present invention there is provided apparatus for use in a method for maintaining the disinfection of a flexible medical endoscope having internal channels, as hereinbefore described, said apparatus including a conditioning station, comprising:
  a reservoir for disinfectant fluid;
  connectors, in communication at one end thereof with the reservoir and adapted at the other end thereof for connection to the internal channels of the endoscope;
  a pump associated with the reservoir and adapted to deliver the disinfectant fluid from the reservoir, through the connectors, and into the endoscope channels; and
  suction means, adapted for connection to a valve of a pouch having a substantially air-tight seal, and further adapted to enable substantial reduction of pressure within the pouch, thereby effecting partial evacuation of said pouch.

The conditioning station preferably further comprises means for flushing the internal endoscope channels with pressurised filtered air, thereby to expel disinfectant fluid from said channels.

As noted above, the present invention is intended primarily for use with flexible medical endoscopes having a plurality of internal channels, comprising an air channel, a water channel and an aspiration channel. The conditioning station therefore preferably comprises a plurality of connectors, each adapted for connection to a dedicated individual internal channel of an endoscope having a plurality of internal channels, comprising an air channel, a water channel and an aspiration channel. In such embodiments, the disinfectant fluid reservoir preferably communicates with the plurality of connectors via a manifold connection.

The conditioning station preferably further comprises a processor adapted to control operation of the reservoir pump and suction means according to a pre-programmed sequence. The conditioning station may also further comprise a printer in communication with the processor.

In preferred embodiments, the apparatus of the invention also includes a pouch having a substantially air-tight seal, said pouch being adapted to house a flexible medical endoscope. The pouch preferably has two substantially air-tight seals, which may utilise plastic zip fasteners and/or an adhesive closure strip. The pouch preferably further comprises a valve adapted for connection to the suction means.

The apparatus may also preferably include a moulded tray shaped to accommodate a flexible medical endoscope, and optionally a liner for said tray.

An absorbent pad is preferably provided for collection of disinfectant fluid expelled from the endoscope channels.

The apparatus preferably further comprises a rigid case, adapted to house and protect the evacuated pouch containing said endoscope.

In order that the present invention may be more clearly understood, a preferred embodiment thereof will now be described in detail, though only by way of example, with reference to the accompanying drawings in which.

Figure 1:
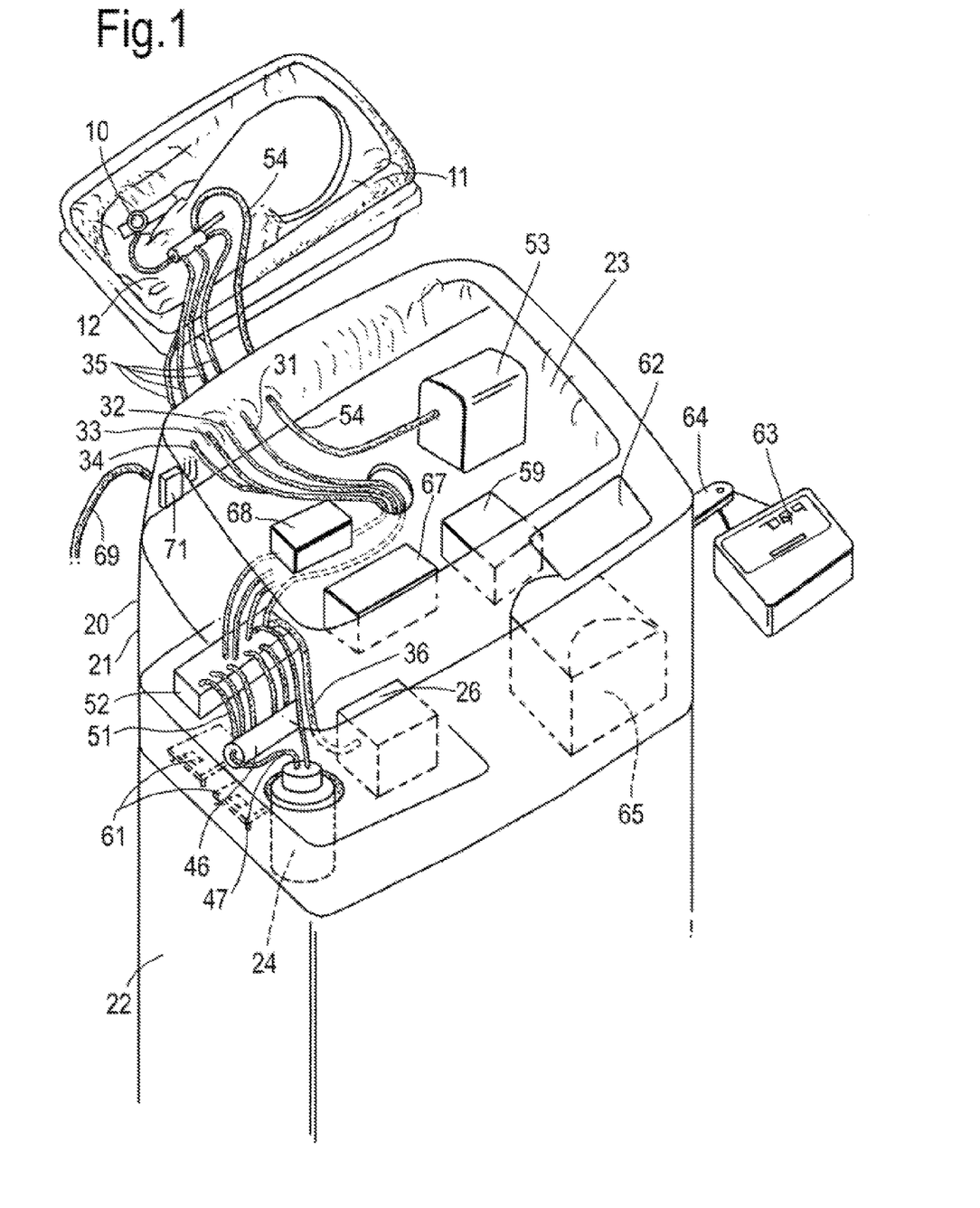
FIG. 1 is a perspective, partially cut-away view of a conditioning station for use in a method for conditioning a flexible medical endoscope, according to the present invention.

Referring first to FIG. 1, there is shown a flexible medical endoscope 10 having been processed to a state of high level disinfection, and ready for treatment by a method according to the first aspect of the present invention. The endoscope 10 is located in a moulded tray 11 shaped so as to protect the endoscope channels 12 and provided with a liner 13, as can be seen best from FIGS. 3 to 5. The lined tray 11 is used to transport the endoscope 10 from the processing area to a conditioning station 20 constituting apparatus according to the second aspect of the present invention.

The conditioning station 20 comprises a housing 21 mounted on a base 22 which may conveniently be provided with wheels to enable the station 20 to be easily moved from one location to another. As can best be seen from FIGS. 3 and 4, the top of the conditioning station forms a working surface 23 adapted to receive the endoscope tray 11 for performance of the method of the present invention.

Figure 2:
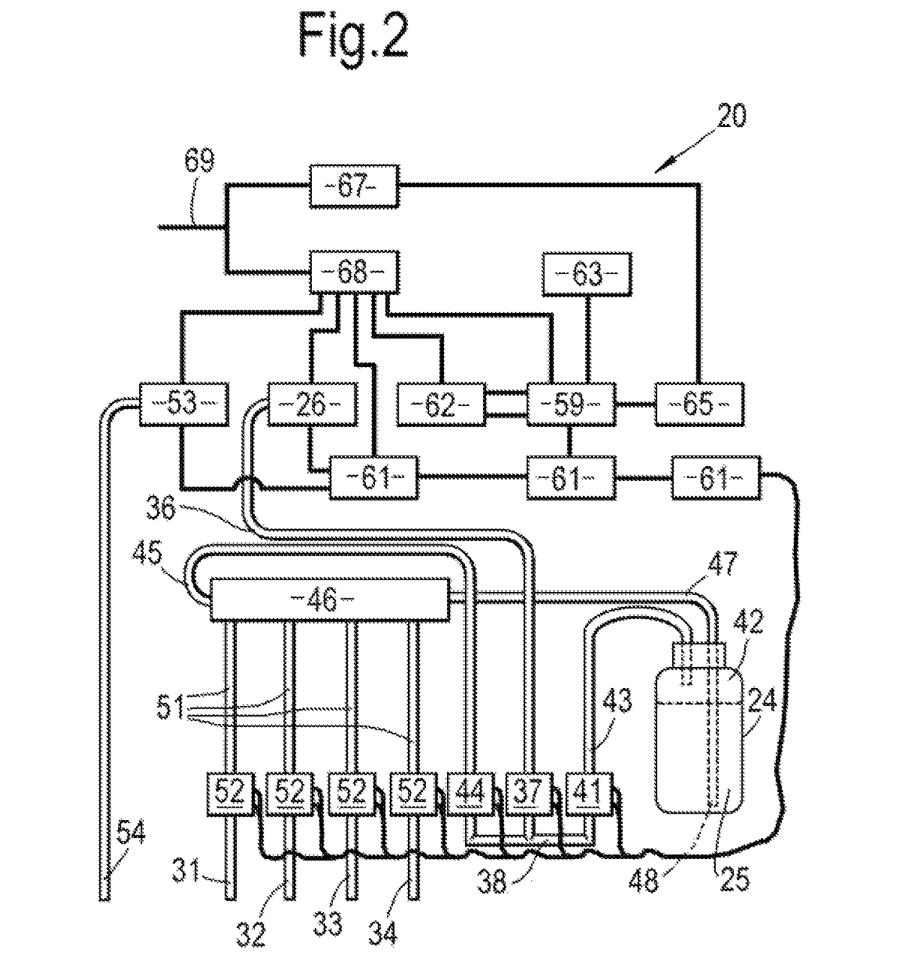
FIG. 2 is a schematic representation of the components of the conditioning station of FIG. 1.

Within the housing 21 are located the operational components of the conditioning station 20, which are also shown in schematic form in FIG. 2. A reservoir 24 is provided which, when the conditioning station 20 is in use, will contain a disinfectant fluid 25 comprising an aqueous solution of hydrogen peroxide, optionally having colloidal silver suspended therein. A reservoir pump 26 is associated with the reservoir 24 and is adapted to enable delivery of the disinfectant fluid 25 to connectors 31-34, each adapted for connection to a specific internal channel of the endoscope 10.

The connectors 31-34 comprise: an air channel connector 31 for connection to the air channel of the endoscope 10; a water channel connector 32 for connection to the water channel of the endoscope 10; an aspiration channel connector 33 for connection to the aspiration channel of the endoscope 10;

and an auxiliary channel connector 34 for connection to the auxiliary channel of the endoscope 10. As can best be seen from FIG. 3, delivery of the disinfectant fluid 25 from each of the connectors 31-34 to the corresponding internal channel of the endoscope 10 is achieved via flexible tubing 35.

As can best be seen from FIG. 2, a first air conduit 36 connects the reservoir pump 26 to an air inlet valve 37 of a three-way valve system 38. A first air outlet valve 41 of the valve system 38 is connected to an air space 42 at the top of the reservoir 24, via a second air conduit 43. A second air outlet valve 44 of the valve system 38 is connected via a third air conduit 45 to a manifold connection 46. A first fluid conduit 47 also connects the reservoir 24 to the manifold 46, and as can be seen from FIG. 2, has an open end 48 submerged in the disinfectant fluid 25. Further fluid conduits 51 then lead from the manifold to fluid valves 52 associated with each of the connectors 31-34.

Figure 5:
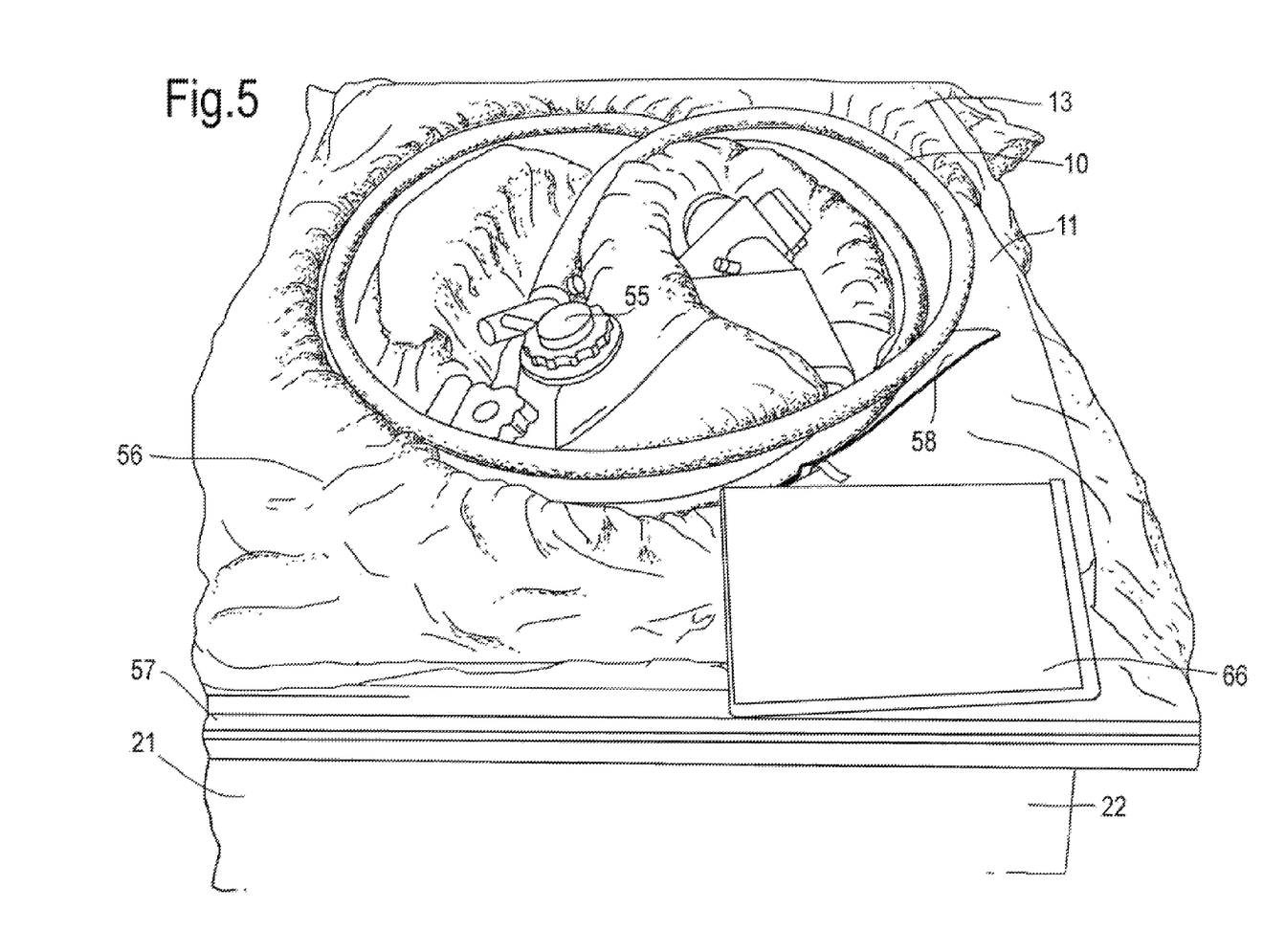

The housing 21 of the conditioning station 20 also houses suction means in the form of a vacuum pump 53, adapted to connect via vacuum tubing 54 to a valve 55 of a pouch 56, within which the endoscope 10 and tray 11 are stored during later stages of the method of the present invention, as is best shown in FIG. 5. The pouch 56 is provided with an air-tight seal 57 in order that the endoscope 10 can be isolated within the pouch 56. As can also be seen in FIG. 5, an absorbent pad 58 is provided within the tray 11 within the pouch 56 to collect fluid 25 expelled from the endoscope 10 during the method of the present invention.

Figure 4:
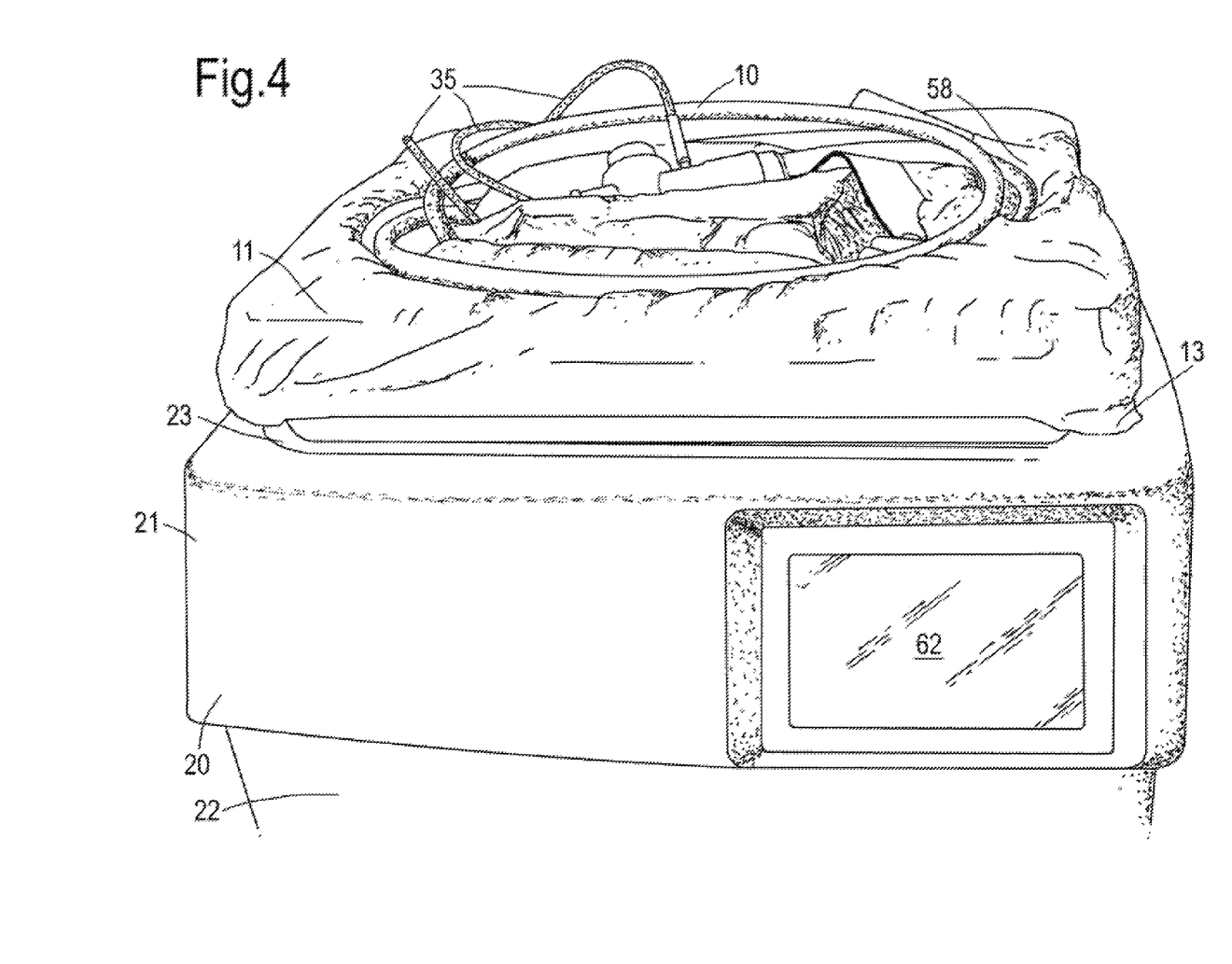

The operation of the reservoir pump 26, the vacuum pump 53, the three-way valve system 38 and the fluid valves 52 is controlled by a microprocessor 59 according to a pre-programmed sequence, the microprocessor 59 being housed internally within the housing 21. The circuitry by which the microprocessor 59 is connection to each of the aforementioned components, via printed circuit boards 61 is illustrated in FIG. 2. Operation of the microprocessor 59 is effected and monitored via a touch screen 62, located on the outside of the housing 21, as illustrated in FIG. 4, and a keyboard 63. The keyboard 63 is usually stored within the housing 21 but can be mounted on a folding arm 64 to be brought out of the housing 21 as required, as illustrated in FIG. 1. The microprocessor 59 is also connected to a printer 65 for generation of a printed label 66 to be attached to the pouch 56 at the end of the method of the present invention, as shown in FIG. 5. The printer 65 is powered by a 24V power supply 67, as illustrated in FIG. 2, whilst the remainder of the electrical components within the housing 21 are powered by a 12V power supply 68. Both the 24V power supply 67 and the 12V power supply 68 are supplied by a mains feed 69 via a power switch 71, as shown in FIG. 1.

A method, according to the present invention, of conditioning a flexible medical endoscope 10 so as to maintain disinfection thereof will now be described, with reference simultaneously to all of FIGS. 1 to 5.

Figure 3:
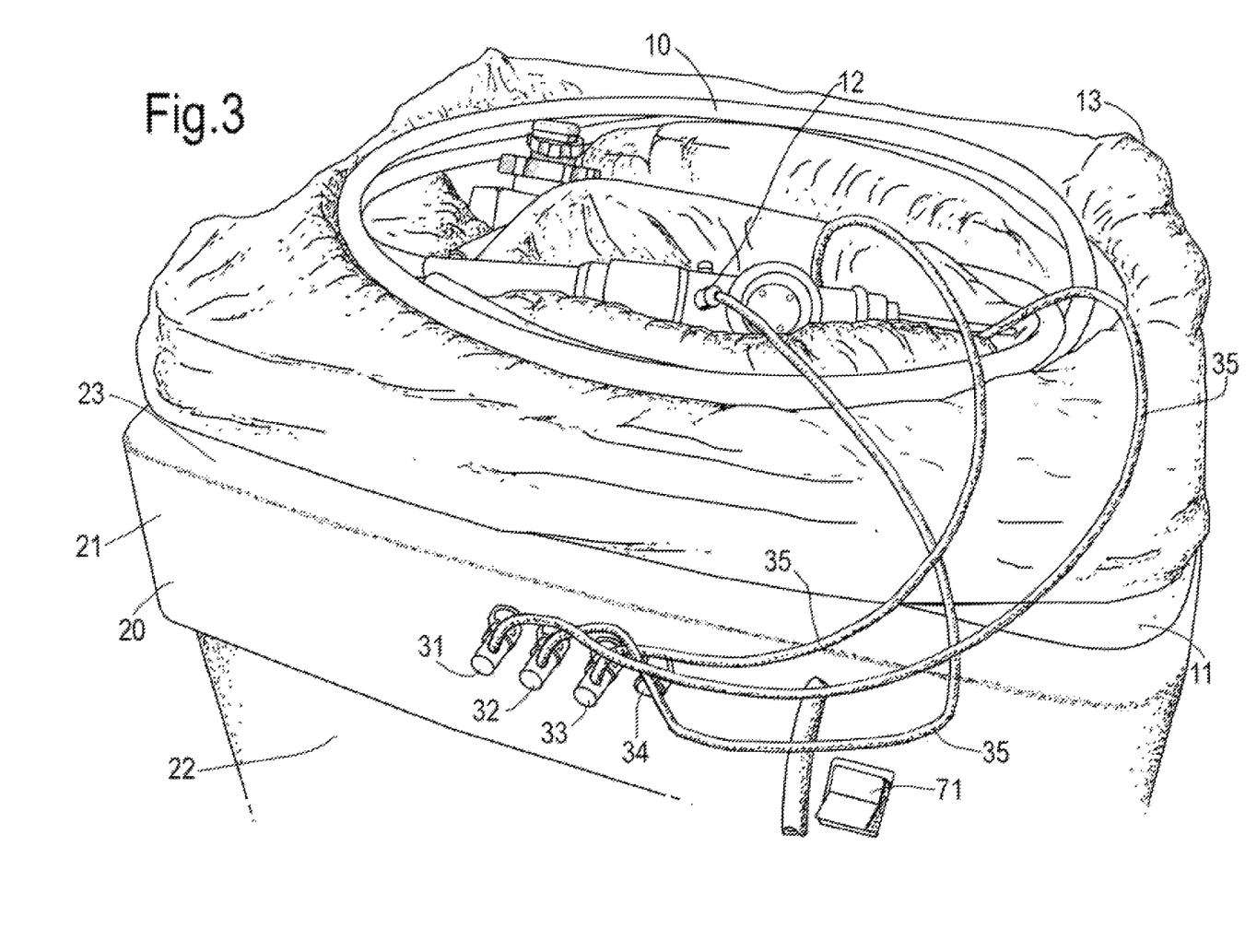
FIGS. 3 to 5 are perspective views of a flexible medical endoscope at the conditioning station of FIGS. 1 to 2, being treated according to the method of the present invention.

Following processing to a state of high level disinfection, the endoscope is placed in the tray 11, which has been fitted with the liner 13. An absorbent pad 58 is placed with the endoscope 10 in the lined tray 11 to collect disinfectant fluid 25 during the condition process. The tray is then brought to the conditioning station 20 and placed on the working surface 23. Next, the internal channels 12 of the endoscope 10 are connected to their respective connector 31-34 on the disinfection maintenance station 20 via flexible tubing 35, as is best shown in FIG. 3. Thus, the air channel of the endoscope 10 is connected to the air channel connector 31; the water channel of the endoscope 10 is connected to the water channel connector 32; the aspiration channel of the endoscope 10 is connected to the aspiration channel connector 33; and the auxiliary channel of the endoscope 10 is (optionally) connected to the auxiliary channel connector.

The microprocessor 59 of the conditioning station 20 is then activated via the touch screen 62, by means of which the user can select one of a number of pre-programmed sequences for conditioning the endoscope 10. The microprocessor 59 then controls operation of the reservoir pump 26, the inlet 37 and first outlet 41 of the three-way valve system 38, so as to force air into the air space 42 at the top of the reservoir 24. This pressurises the air space 42, thus causing the disinfectant fluid 25 to flow through the manifold connection 46 to the fluid valves 52 associated with each of the channel connectors 31-34. Operation of each of the fluid valves 52 is also controlled by the microprocessor 59 so as to flush each of the endoscope channels 12 in turn with disinfectant fluid 25 according to the selected pre-programmed sequence.

Once all of the channels 12 have been flushed with disinfectant fluid 25, or after an optional time delay depending on the selected sequence, the microprocessor 59 then operates the reservoir pump 26 again, this time in combination with the inlet 37 and second outlet 44 of the three-way valve system 38, so as to force air through the manifold connection 46 to the fluid valves 52. Operation of each of the fluid valves 52 is again controlled by the microprocessor 59 so as to flush each of the endoscope channels 12 in turn with dry filtered air (the filter being incorporated within the reservoir pump 26) according to the selected pre-programmed sequence, so as to expel the disinfectant fluid 25 from the channels 12. The disinfectant fluid 25 expelled from the endoscope channels 12 is collected on the absorbent pad 58. The flexible tubing 35 connecting the endoscope channels 12 to the channel connectors 31-34 is then disconnected.

Next, the lined tray 11 containing the endoscope is placed into the pouch 56, which is then sealed by means of the air tight seal 57. The vacuum tubing 54 is then connected to the valve 55 of the pouch 56, and the vacuum pump 53 is activated, via the touch screen 62 and microprocessor 59, in order partially to evacuate the pouch 56. This provides a substantially sterile atmosphere by removing air from the pouch, thus significantly reducing, or ideally preventing, the multiplication of aerobic bacteria within the pouch 56. In addition, the reduction of air pressure within the pouch 56 has the effect of drawing any residual disinfectant fluid 25 out of the endoscope channels 12 onto the absorbent pad 58. Maintaining the reduced pressure over an extended time period then also causes the disinfectant fluid 25 to evaporate from the pad 58 into the pouch 56, thus enabling coating of the external surfaces of the endoscope 10 with the disinfectant fluid 25, thus providing a further disinfectant effect.

Once the partial evacuation of the pouch 56 has been effected, for a pre-determined time period or to a pre-determined air pressure, according to the selected sequence, the vacuum pump 53 is deactivated and the vacuum tubing 54 disconnected from the pouch valve 55. The microprocessor 59, via the printer 65, then generates a printed label 66, identifying the serial number of the endoscope 10, its disinfection status, and the estimated maximum disinfection maintenance period. The label 66 is then applied to the partially evacuated pouch 56, as shown in FIG. 5, and the isolated endoscope 10 within the lined tray 11, within the pouch 56, is ready for prolonged storage.

The invention claimed is:
1. Apparatus for use in a method of conditioning a flexible medical endoscope having internal channels, so as to maintain disinfection of said endoscope following processing to a state of high level disinfection, said apparatus including a conditioning station, comprising:

a reservoir for disinfectant fluid; connectors, in communication at one end thereof with the reservoir and adapted at the other end thereof for connection to the internal channels of the endoscope; a pump associated with the reservoir and adapted to deliver the disinfectant fluid from the reservoir, through the connectors, and into the endoscope channels; and suction means, adapted for connection to a valve of a pouch having a substantially air-tight seal, and further adapted to enable substantial reduction of pressure within the pouch, thereby effecting partial evacuation of said pouch.

2. The apparatus as claimed in claim 1, further comprising means for flushing the internal endoscope channels with pressurised filtered air, thereby to expel disinfectant fluid from said channels.

3. The apparatus as claimed in claim 1, wherein the conditioning station comprises a plurality of connectors, each adapted for connection to an individual dedicated internal channel of an endoscope having a plurality of internal channels, comprising an air channel, a water channel and an aspiration channel, and wherein the disinfectant fluid reservoir communicates with the plurality of connectors via a manifold connection.

4. The apparatus as claimed in claim 3, wherein the conditioning station comprises an auxiliary channel.

5. The apparatus as claimed in claim 1, wherein the conditioning station further comprises a processor adapted to control operation of the reservoir pump and suction means according to a pre-programmed sequence and a printer in communication with the processor.

6. The apparatus as claimed in claim 1, further comprising a pouch having two substantially air-tight seals and comprising a valve adapted for connection to said suction means, said pouch being adapted to house a flexible medical endoscope.

7. The apparatus as claimed in claim 1, further comprising a molded tray shaped to accommodate a flexible medical endoscope.

8. The apparatus as claimed in claim 1, further comprising an absorbent pad for collection of disinfectant fluid expelled from the endoscope channels.

9. The apparatus as claimed in claim 1, further comprising a rigid case, adapted to house and protect the evacuated pouch containing said endoscope.

10. The apparatus as claimed in claim 1, further comprising
a pump which following charging of the internal channels in turn according to a pre-determined sequence with disinfectant fluid, is configured to flush said internal channels with pressurized filtered air so as to expel disinfectant fluid from said internal channels;
a pouch having a substantially air-tight seal and a valve enabling connection to suction means;
an absorbent pad being arranged to collect disinfectant fluid expelled from the internal channels and wherein the reduction of pressure within the pouch is sufficient to cause evaporation of disinfectant fluid collected on the absorbent pad, thereby enabling coating of the external surfaces of the endoscope with said evaporated disinfectant fluid;
a printed label configured to be applied to the pouch, said label identifying the endoscope, its conditioned status, and an estimated maximum conditioned maintenance period; and
wherein the connectors are dedicated connectors, in communication at one end thereof with the disinfectant reservoir and adapted at the other end thereof for connection to the internal channels of the endoscope enabling fluid communication.

11. The apparatus as claimed in claim 1, wherein the disinfectant fluid comprises a dilute aqueous solution of hydrogen peroxide having a concentration in the range of from 0.5% to 1.5% by weight.

12. The apparatus as claimed in claim 11, wherein the dilute aqueous solution of hydrogen peroxide has a concentration of substantially 1.4% by weight.

13. The apparatus as claimed in claim 1, wherein the disinfectant fluid further comprises colloidal silver.

* * * * *